ized. The fermentation is effected at a temperature between 20° and 40° C for from 12 to 48 hours, on which, if desired, the fermented material is dried.

United States Patent [19]
Hansen

[11] 4,008,334
[45] Feb. 15, 1977

[54] PROCESS FOR REMOVAL OF WATER-SOLUBLE CARBOHYDRATES IN THE PRODUCTION OF PLANT PROTEIN PRODUCTS

[75] Inventor: Ole Kaae Hansen, Aarhus, Denmark

[73] Assignee: Aarhus Oliefabrik A/S, Aarhus, Denmark

[22] Filed: June 3, 1975

[21] Appl. No.: 583,164

[30] Foreign Application Priority Data

June 5, 1974 United Kingdom ............. 24845/74

[52] U.S. Cl. .................................. 426/46; 426/52; 426/44

[51] Int. Cl.² ......................................... A23L 1/20

[58] Field of Search ................. 426/44, 46, 49, 52; 195/4

[56] References Cited

UNITED STATES PATENTS

| 2,930,700 | 3/1960 | Bradof ................................ 426/46 |
| 3,632,346 | 1/1972 | Sherba ................................. 426/46 |
| 3,803,329 | 4/1974 | Valentas et al. ..................... 426/44 |
| 3,810,997 | 5/1974 | Chien ................................... 426/49 |
| 3,912,818 | 10/1975 | Chandler et al. .................... 426/46 |
| 3,912,821 | 10/1975 | Chandler et al. .................... 426/46 |

*Primary Examiner*—A. Louis Monacell
*Assistant Examiner*—C. A. Fan
*Attorney, Agent, or Firm*—Lewis H. Eslinger

[57] ABSTRACT

This invention provides a method for removal of all water soluble carbohydrates in the production of plant protein products, including oligosaccharides containing alpha-1,6-galactosidic bonds which are known to cause flatulence in man and animals. In the method an aqueous solution or dispersion of the plant protein material containing 1–60%, and preferably 15–50% of the dry matter is fermented with particular strains of Saccharomyces that have been found to degrade and assimilate flatus-causing carbohydrates. The fermentation is effected at a temperature between 20° and 40° C for from 12 to 48 hours, on which, if desired, the fermented material is dried.

13 Claims, No Drawings

PROCESS FOR REMOVAL OF WATER-SOLUBLE CARBOHYDRATES IN THE PRODUCTION OF PLANT PROTEIN PRODUCTS

The present invention relates to a method for removal of water-soluble carbohydrates in the production of plant protein products, more specific removal of water-soluble carbohydrates causing flatulence in man and animals.

The term water-soluble carbohydrates as employed herein includes as well such carbohydrates that are also soluble in aqueous solutions of ethanol such as glucose, galactose, sucrose, raffinose and stachyose.

The term plant protein products as employed herein refers to all such products as meal, grits, milk concentrates and isolates that are produced from plants rich in protein such as soybean, rapeseed, navy beans, lima beans, cottonseed, peanut etc., and containing protein as a predominant constituent.

The use of such plant protein products for food and feed purpose is well known and advantageous on account of their low price compared with their high nutritional value and desirable functional properties. The ingestion of many plant protein products is, however, known to cause flatulence in man and animals. This flatulence formation is today known to be caused by carbohydrates containing one or more $\alpha$-1,6-galactosidic bonds, such as stachyose and raffinose (see e.g. Rackis et al., J. Agr. Food Chem. 18(6), 977–982 (1970)).

The reason for the flatus-effect of these carbohydrates is that neither man nor animals possess enzyme systems capable of degrading the $\alpha$-1,6-galactosidic bonds. Consequently, such carbohydrates are carried undigested to the intestine where they are finally fermented by the bacteria flora normally present therein. This fermentation results in the production of large amounts of gas, thus causing flatulence and serious discomfort in man and animals.

Therefore, it is obvious that the acceptability of plant protein products for food or feed purpose depends on the absence of significant amounts of such carbohydrates.

The original material for the manufacturing of plant protein products normally contain 5 – 15% of such carbohydrates, mainly as the tetrasaccharide stachyose and the trisaccharide raffinose, but also other $\alpha$-1,6-galactosides like verbascose and melibiose are frequently present.

Various methods are known for production of plant protein products with reduced content of these flatus-causing carbohydrates.

Thus it has been proposed to hydrolyze them to non-flatus-causing carbohydrates by the addition of specific $\alpha$-galactosidase enzyme preparations to an aquous solution or dispersion of the carbohydrate containing material This method has, however, several disadvantages. Primarily, such enzyme preparations are very expensive and thus ineconomical in use. Secondly, the proteinase frequently found as an accompanying activity is in general highly undesirable for this purpose, a fact that limits the number of suitable enzyme preparations. Furthermore, it is often disadvantageous that the enzyme treatment do not reduce the total amount of carbohydrate present, but only hydrolyze the flatus-causing carbohydrates to other carbohydrates with lower molecular weight, which may eventually promote growth of microorganisms and browning reactions in the manufacturing process.

Still another disadvantage has been reported, namely that the taste of the final product after the enzyme treatment was found to be extremely bad (see Calloway et al., J. Food Sci. 36, 251–255 (1970)).

Another known method for reducing the amount of flatus-causing carbohydrates is to produce protein concentrates or isolates. Thus, by the manufacturing of concentrates the said carbohydrates are removed by extraction with either acid, water or aquous solutions of ethanol. The process is carried out in such a way that the proteins remain undissolved together with polysaccharides during the extraction.

In contrary, by the manufacturing of protein isolates the conditions are chosen so that the proteins dissolve together with the water-soluble carbohydrates in an aquous extraction step, thus separating them from the polysaccharides not soluble in water. In the following step, the proteins are separated from the water-soluble carbohydrates by acid precipitation at the isoelectric pH value.

Thus, the content of flatus-causing carbohydrates as well as other water-soluble carbohydrates is substantially reduced by the production of protein concentrates and isolates. Hitherto, however, the disposal problem of the whey, i.e. the by-product containing the water-soluble carbohydrates, has been a serious obstacle to an economical production of concentrates and isolates (see Meyer, J.Am. Oil Chem. Soc. 48(9), 484–488 (1971) and Wilcke, J. Am. Oil Chem. Soc. 51, 197 A–177 A (1974)).

In contrast to the hitherto known methods as mentioned above, the present invention constitutes a novel means whereby the said flatus-causing carbohydrates as well as other water-soluble carbohydrates normally present can be completely eliminated. According to the invention the production of plant protein products with a negligible content of water-soluble carbohydrates is thus possible without having the problem of whey disposal.

According to the invention the removal of water-soluble carbohydrates is carried out by fermentation of the carbohydrate-containing material by means of particular strains of Saccharomyces such as baker's yeast, i.e. *Saccharomyces cerevisiae*, wine yeast, i.e. *S. cerevisiae var. ellipsoideus*, or brewer's yeast, i.e. *S. carlsbergensis*. In a screening programme for suitable microorganisms it was namely found that among all the species tested, particular strains of the above mentioned *Saccharomyces* species were the only ones capable of degrading the flatus-causing carbohydrates. In fact, not only did they degrade and assimilate these flatus-causing carbohydrates, but they degraded and assimilated all other water-soluble carbohydrates present in soybean meal as well, leaving at the end of the fermentation period no trace of carbohydrates detectable on a thin layer chromatogram (TLC) run as mentioned below. Regarding *S. cerevisiae*, this invented ability to completely degrade and digest carbohydrates containing $\alpha$-1,6-galactosidic bonds is to the best of our knowledge in contrast to what has earlier been reported on this species (see Holger Jorgensen: Teknisk Biokemi, Vol. 1, p. 49, Copenhagen 1956, or Gibbs & Shapton: Identification Methods for Microbiologists, Vol. B, Academic Press 1968, or Adams et al., JACS 65, 1369 (1943).

In a few existing patents treatment of vegetable material with *Saccharomyces* species is claimed. Thus U.S. Pat. No. 2,930,700, filed Nov. 1, 1957 by the Wander Co., claims a process for improving the flavour of soy flour which comprises mixing soy flour with water and yeast. The process temperatures prescribed herein are, however, so high that the yeast is rapidly killed, and the reaction time is too short to effectuate any substantial reduction of the concentration of raffinose and stachyose.

U.S. Pat. No. 3,803,329, filed May 10, 1971 by General Mills Inc., claims a method for producing a bland textured soy protein comprising fermentation with yeast. The water content of the substrate prescribed herein is, however, too low to obtain the object of the present invention. It is clearly demonstrated by the present invention that by employing such low water contents the fermentation stops before the concentration of raffinose and stachyose has been substantially reduced.

U.S. Pat. No. 3,810,997, filed Oct. 7, 1971 by Kraftco Corp., claims a method for improving the flavour of soy beans by yeast fermentation. Neither in this patent the object is complete removal of oligosaccharides and thus the importance of selecting a strain having this particular ability is not emphasized. In any case, the fermentation period prescribed herein is too short to obtain any substantial reduction in the concentration of raffinose and stachyose.

In contrast to the above mentioned patents the present invention stresses the importance of a careful selection of both the Saccharomyces strain and the fermentation conditions employed in order to obtain complete removal of oligosaccharides.

By means of the TLC test mentioned below it has clearly been demonstrated by the present inventor that the Saccharomyces metabolisation of the various oligosaccharides is sequential, i.e. as long as any sucrose remains, raffinose and stachyose are not degraded or assimilated. Therefore any partial reduction of the oligosaccharides concentration is primarily caused by the removal of sucrose and not stachyose or raffinose.

A particular advantage of this invention is that the removal of the said carbohydrates is carried out by means of microorganisms that are already accepted and in general use for production of foodstuffs, and which may be incorporated into these, if desired.

According to the invention the material from which removal of the said carbohydrates is wanted, should be in an aquous solution or dispersion containing 1 – 60% dry matter, preferably 15 – 50%, and 0.5 – 20% water-soluble carbohydrates, preferably 5 – 15%, before the fermentation is initiated. At concentrations higher than 60% dry matter the removal of the flatus-causing carbohydrates was invariably found to be incomplete.

During the end of the fermentation, an appropriate yeast concentration is $10^7 - 10^{10}$ cells/g substrate. The optimal yeast concentration depends on the actual substrate and the fermentation time available. Normally, a cell concentration of $10^8 - 10^9$/g substrate is suitable.

The fermentation should preferably be carried out in closed vessels to ensure sterility. In order to decrease the fermentation period sterile air in amounts of 0.1 – 2 volumes per volume of substrate per minute may be blown through the substrate. The temperature should be between 20° and 40° C, preferably 28°– 37° C. pH is adjusted in the range of 4 – 7, preferably pH 4.5 – 5.0.

Depending on the nature of the carbohydrate containing starting material, supplementing nutrients may be added to the substrate - such as nitrogenous, phosphorous, and sulphurous compounds, trace minerals, nucleotides and vitamins. Furthermore, enzymes such as proteases and cellulases may be added to the substrate. In case of excess foaming tendency, antifoaming agents such as silicone oils or polyglycols may be added.

The fermentation may be carried out either batchwise or continuous.

In batch fermentations a pure yeast culture is propagated through appropriate steps to the main fermenter containing the sterilized or pasteurized carbohydrate-containing substrate. This substrate is seeded with inoculum sufficient to reach an initial cell concentration of at least $10^6 - 10^8$/g substrate. Using such an amount of inoculum, the content of carbohydrates are in the course of 12 – 48 hours of fermentation reduced to such a level that the TLC test mentioned below is negative.

In continuous fermentation no propagation step is necessary. This, in addition to labour savings and greater productivity makes the continuous process economically attractive compared with batch fermentation.

The process according to this invention can be applied either as a substitute for the traditional methods of producing the said plant protein products, or it can be used in combination with the hitherto known methods of producing the said plant protein products.

By means of the said process plant protein products having bland taste, good functional properties and high nutritive value are obtained. Not only are the flatus-causing carbohydrates removed but also other anti-nutritional factors such as phytic acid are destroyed. Thus the protein products are equally suited for food and feed purpose.

Water-soluble carbohydrates were identified by means of thin layer chromatography (TLC) on silica gel plates, applying 1 $\mu$l of the solution containing the carbohydrates to be analyzed. As solvent was used n-butanol:pyridin:water in the proportions 6:4:3. The spots were developed by spraying with diphenylamine-anilin-phosphoric acid in aceton, followed by incubating for 10 minutes at 105° C. Carbohydrates remaining appeared as brownish spots.

The quantitative determination of water-soluble carbohydrates was made by means of colorimetry using the phenol-sulphuric reaction according to Dubois et al. (see Anal. Chem. 28(3), 350 (1956)).

EXAMPLE 1

20 g - portions of defatted soybean meal were suspended in 100 ml of tap water in 300 ml conical flasks with caps. The suspensions were boiled for 15 min., cooled to 30° C and each seeded with a loopful of pure cultures of one of the microorganism species mentioned below, all of which showed negligible proteolytic activity.

After an appropriate incubation period the broths were centrifuged and the content of carbohydrates in the supernatant was examined by TLC. The results of this test are shown in table L.

A + sign in the table means that the spot reaction is positive. Thus it will be seen from the table that *Saccharomyces cerevisiae* (baker's yeast) and certain strains of *S. carlsbergensis* and *S. cerevisiae var. ellipsoideus* were the only ones of the microorganisms tested able to remove all the flatus-causing carbohydrates. In addition, sucrose and other water-soluble carbohydrates present in soybean meal was removed as well. Disappearance of the carbohydrate spots means that the concentration level during the fermentation has been reduced from approximately 10% in the starting dry material to less than 1%.

Table 1.

Removal of carbohydrates from soybean meal.

| Type of microorganism | Time of incubation | Residual carbohydrates | | | |
|---|---|---|---|---|---|
| | | sucrose | raffinose | stachyose | others |
| S. carlsbergensis (strain Ceres F) | 18 h | − | − | + | + |
| S. carlsbergensis (strain DGI F216) | 18 h | − | − | − | − |
| S. cerevisiae var. ellipsoideus, (BB Wine yeast, 7 strains) | 18 H | − | + | + | + |
| S. cerevisiae var. ellipsoideus, (BB wine yeast, 1 strain: sauterne) | 18 h | − | − | − | − |
| S. cerevisiae (DDSF maltesergaer) | 18 h | − | − | − | − |
| S. fragilis[x] | 18 h | − | + | + | + |
| Aspergillus niger[x] | 96 h | + | + | + | + |
| Aspergillus oryzae[x] | 96 h | + | + | + | + |
| Aspergillus awamori[x] | 96 h | − | + | + | + |
| Bacillus subtilis[x] | 18 h | + | + | + | + |
| None | 0 h | + | + | + | + |

[x]A/S Grindstedvaerket's Culture Collection

EXAMPLE 2

10 kg of defatted soybean meal was suspended into 65 liter of tap water. pH in this substrate was adjusted to 4.5, boiled for 15 min. and then transferred to a sterile 100 liter fermenter. After cooling to 30° C the substrate was inoculated with 130 g of baker's yeast (Malteserkorsgaer from De Danske Sprit Fabrikker, containing 25% dry material).

The fermentation was carried out under agitation and aeration with ½ volume sterile air per volume substrate per minute. The temperature was maintained at 30° C, and sterile silicone antifoam agent was added when necessary.

After 16 1/2 hours of fermentation the fermenter was stopped and the broth was analyzed for carbohydrates.

The TLC test showed complete disappearance of water-soluble carbohydrates while quantitative analysis showed that the fermentation has removed carbohydrates to the amount of 10% of the starting dry weight material.

EXAMPLE 3

The broth from example 2 was dried in a fluid bed at 105° C and showed a total protein content of 64% compared with 52% in the starting material, based on dry weight. The content of yeast was approximate 1% based on dry weight. The dried material had a light colour, a granular structure and a bland taste. It was readily eaten by dogs and cats in feeding tests. Thus it was found useful as a pet food that could be used either alone or in formulations with known pet-food ingredients.

EXAMPLE 4

Whey from the manufacturing of soy protein concentrate, containing 12.5% of sucrose, 10.0% of stachyose and 2.5% of raffinose was diluted with tap water in the proportion 1 volume of whey to 4 volumes of water. The resulting diluted whey was adjusted at pH 4.5 with sulphuric acid and heated to boiling. After cooling 50 ml thereof was inoculated with baker's yeast to a cell concentration of $10^6$/ml substrate.

After aerobic fermentation for 24 hours at 30° C on a magnetic stirrer the broth was centrifuged and the supernatant examined for carbohydrate content. The TLC-test failed to detect any remaining carbohydrates.

The yield of baker's yeast dry material was found to be 43% based on dry weight of the carbohydrates in the substrate. Baker's yeast produced in this way can be used for similar purposes as baker's yeast grown on conventional substrates.

EXAMPLE 5

To 25 kg of soybean flakes were added 15 liters of water. The mixture was pasteurized for 30 minutes at 65° C. After cooling to 30° C the pasteurized substrate was inoculated with 500 g of baker's yeast suspended in 10 liters of sterile saline water. The yeast suspension was sprayed on the substrate while agitating in a conventional mixer. The inoculated substrate was fermented for 24 hours at 35° C. Thereafter it was pasteurized by vacuum drying at 65° C and finally milled. The resulting product contained 64% of protein in the dry matter and no trace of water-soluble carbohydrates. The colour of the powder was yellowish white and the taste was bland.

EXAMPLE 6 (Reference)

An experiment was carried out according to U.S. Pat. No. 3,810,997. 10 g of defatted soybean meal was suspended in 100 ml of tap water and inoculated with 0.8 g of compressed baker's yeast. After 4 hours of aerated fermentation the suspension was pasteurized by heating to 77° C. After cooling the protein was precipitated with acid to pH 4.5 and removed by centrifugation. The supernatant was examined by the TLC-sugar test which showed that only sucrose was removed during the fermentation. The content of raffinose and stachyose remained almost unchanged.

EXAMPLE 7 (Reference)

An experiment was carried out according to U.S. Pat. No. 3,803,329. 100 g of pasteurized and defatted soybean meal was carefully mixed with 2.5 g of compressed baker's yeast suspended in 0.9% sterile saline water to make a final moisture content of 27% in the mixture. The fermentation was run for 48 hours at room temperature. The TLC-sugar test showed no detectable reduction in the concentration of water soluble carbohydrates.

What I claim is:

1. Process for removal of water-soluble carbohydrates in the production of plant protein products in which an aqueous solution or dispersion of the carbohydrate-containing material containing 1–60% dry matter is inoculated with a microorganism selected from the genus Saccharomyces and having the ability to degrade and assimilate flatus-causing carbohydrates and fermented for from 12 to 48 hours at a temperature of 20° to 40° C and at a pH of from 4 to 7 to remove substantially all water-soluble carbohydrates.

2. Process according to claim 1, in which the microorganism is S. cerevisiae strain DDSF maltersergaer.

3. Process according to claim 1, in which the microorganism is S. carlsbergensis strain DGI F216.

4. Process according to claim 1, in which the microorganism is S. cerevisiae var. ellipsoideus strain BB sauterne.

5. Process according to claim 1, in which the aqueous solution or dispersion contains 15–50% dry matter.

6. Process according to claim 1, in which the aqueous solution or dispersion contains 0.5–20% of water-soluble carbohydrates before the fermentation is initiated.

7. Process according to claim 6, in which the aqueous solution or dispersion contains 5–15% of water-soluble carbohydrates.

8. Process according to claim 1, in which the temperature is from 28° to 37° C.

9. Process according to claim 1, in which the pH is adjusted in the range of 4.5–5.0.

10. Process according to claim 1, in which the substrate is seeded with sufficient inoculum to reach an initial cell concentration of at least $10^6$–$10^8$ cells per g of substrate.

11. Process according to claim 1, in which sterile air is blown through the substrate in amounts of 0.1–2 volumes per volume of substrate per minute during the fermentation period.

12. Process according to claim 1, in which the fermentation is conducted continuously.

13. Plant protein product produced by the process of claim 1, wherein substantially all water-soluble carbohydrates including the flatus-causing carbohydrates are removed.

* * * * *

UNITED STATES PATENT OFFICE
CERTIFICATE OF CORRECTION

Patent No. 4,008,334     Dated February 15, 1977

Inventor(s) Ole Kaae Hansen

It is certified that error appears in the above-identified patent and that said Letters Patent are hereby corrected as shown below:

Column 1, line 16 after "milk", insert a comma.

Column 1, line 58 after "material", insert a period.

Column 4, line 44 change "aceton" to --acetone--.

Column 4, line 63 change "L" to --1--.

Column 5, Table 1 opposite the third microorganism, change

"18 H" to --18 h--.

Column 7, line 32 change "maltersergaer" to --maltesergaer--.

Signed and Sealed this

Twenty-second Day of November 1977

[SEAL]

Attest:

RUTH C. MASON
*Attesting Officer*

LUTRELLE F. PARKER
*Acting Commissioner of Patents and Trademarks*